(12) United States Patent
Braun et al.

(10) Patent No.: US 8,957,254 B2
(45) Date of Patent: Feb. 17, 2015

(54) PROCESS FOR CHEMICAL SYNTHESIS FROM AN ALKENONE MADE FROM A HALOGENATED PRECURSOR

(71) Applicants: Max Braun, Wedemark (DE); Stefan Palsherm, Barsinghause (DE); Uta Claassen, Hohenhameln (DE); Alain Lambert, Beauvechain (BE)

(72) Inventors: Max Braun, Wedemark (DE); Stefan Palsherm, Barsinghause (DE); Uta Claassen, Hohenhameln (DE); Alain Lambert, Beauvechain (BE)

(73) Assignee: Solvay SA, Brussels (BE)

( * ) Notice: Subject to any disclaimer, the term of this patent is extended or adjusted under 35 U.S.C. 154(b) by 0 days.

(21) Appl. No.: 14/046,171

(22) Filed: Oct. 4, 2013

(65) Prior Publication Data

US 2014/0051892 A1  Feb. 20, 2014

Related U.S. Application Data

(63) Continuation-in-part of application No. 12/999,730, filed as application No. PCT/EP2010/059549 on Jul. 5, 2010, now Pat. No. 8,552,221, which is a continuation-in-part of application No. PCT/EP2009/058525, filed on Jul. 6, 2009.

(30) Foreign Application Priority Data

Jan. 7, 2010 (EP) .................................... 10150229

(51) Int. Cl.
| | |
|---|---|
| *C07C 45/41* | (2006.01) |
| *C07D 211/02* | (2006.01) |
| *C07D 213/64* | (2006.01) |
| *C07D 401/00* | (2006.01) |
| *C07C 45/65* | (2006.01) |

(52) U.S. Cl.
CPC ................. *C07C 45/41* (2013.01); *C07C 45/65* (2013.01)
USPC ........ 568/392; 568/394; 546/249; 546/276.1; 546/298

(58) Field of Classification Search
CPC ........ C07C 45/41; C07C 45/65; C07C 45/455
USPC ................ 568/392, 394; 546/249, 276.1, 298
See application file for complete search history.

(56) References Cited

U.S. PATENT DOCUMENTS

| 5,708,174 | A | 1/1998 | King et al. |
|---|---|---|---|
| 5,708,175 | A | 1/1998 | Koyanagi et al. |
| 6,428,199 | B1 | 8/2002 | Rupaner et al. |
| 7,057,079 | B2 | 6/2006 | Braun et al. |
| 7,405,328 | B2 | 7/2008 | Hausmann et al. |
| 8,076,487 | B2 | 12/2011 | Takabe et al. |
| 8,426,650 | B2 | 4/2013 | Braun et al. |
| 8,431,710 | B2 | 4/2013 | Braun |
| 8,440,865 | B2 | 5/2013 | Braun et al. |
| 8,519,195 | B2 | 8/2013 | Braun et al. |
| 2004/0224960 | A1 | 11/2004 | Borchardt et al. |
| 2006/0084813 | A1 | 4/2006 | Hausmann et al. |
| 2006/0128702 | A1 | 6/2006 | Pal et al. |
| 2006/0198771 | A1 | 9/2006 | Devic |
| 2009/0005603 | A1 | 1/2009 | Bland |
| 2009/0029863 | A1 | 1/2009 | Nugent et al. |
| 2009/0221618 | A1 | 9/2009 | Arista et al. |
| 2009/0318455 | A1 | 12/2009 | Kossen et al. |
| 2010/0004457 | A1 | 1/2010 | Bland et al. |
| 2010/0222592 | A1 | 9/2010 | Takabe et al. |
| 2011/0021514 | A1 | 1/2011 | Cox et al. |
| 2011/0071291 | A1 | 3/2011 | Ikegami et al. |
| 2011/0287937 | A1 | 11/2011 | Takabe et al. |
| 2012/0053210 | A1 | 3/2012 | Whitten et al. |
| 2013/0172334 | A1 | 7/2013 | Dart et al. |

FOREIGN PATENT DOCUMENTS

| EP | 0744400 A2 | 11/1996 |
|---|---|---|
| WO | WO 03066558 A2 | 8/2003 |
| WO | WO 2004108647 A2 | 12/2004 |
| WO | WO 2009006217 A1 | 1/2009 |
| WO | WO 2010000871 A2 | 1/2010 |
| WO | WO 2010037688 A1 | 4/2010 |
| WO | WO 2010099922 A1 | 9/2010 |

(Continued)

OTHER PUBLICATIONS

Tietze, L. F., et al—"Synthesis of Alkyl Propanoates by a Haloform Reaction of a Trichloro Ketone: Preparation of Ethyl 3,3-Diethoxypropanoate"; Organic Syntheses, 1990, vol. 69, pp. 238-244, 7 pgs.

(Continued)

*Primary Examiner* — Sikarl Witherspoon
(74) *Attorney, Agent, or Firm* — Beatrice C. Ortego

(57) ABSTRACT

Process for synthesizing a chemical, in particular an agriculturally or pharmaceutically active compound, including: a first step comprising reacting a carboxylic acid halide with a vinyl ether to prepare a halogenated precursor of an alkenone; a second step comprising eliminating hydrogen halide from such precursor to form an alkenone, preferably by thermolysis under specific conditions; and a third step which uses the formed alkenone as a building block to synthesize the chemical. First step may be done in a liquid reaction medium comprising an alkenone or a halogenated alkenone precursor, or in a liquid reaction medium in turbulent state, specifically by creation of gas bubbles of the carboxylic acid halide herein. Second step may include a flash thermolysis, vacuum thermolysis, thermolysis under stripping with inert gas, and/or a thermolysis at a temperature from >90° C. to 120° C. Third step preferably comprises reacting the alkenone with a nitrogen-containing compound.

17 Claims, No Drawings

(56) References Cited

FOREIGN PATENT DOCUMENTS

WO    WO 2011003854 A1    1/2011
WO    WO 2011003860 A1    1/2011

OTHER PUBLICATIONS

Colla, Agenor, et al—"Trihaloacetylated Enol Ethers—General Synthetic Procedure and Heterocyclic Ring Closure Reactions with Hydroxylamine" Synthesis, Issue 6, Georg Thieme Verlag, Stuttgart University, Jun. 1, 1991, pp. 483-486, 4 pgs.

Tietze, L.-F., et al—"Highly Efficient Syntheses of Alkyl 3,3-Dialkoxypropanoates, Alkyl 4-Ethoxy-2-oxo-3-butenoates, and Monoprotected Malonaldehydes", Synthesis, 1988, vol. 4, pp. 274-277; XP-002587967; 4 pgs.

Xin, Y., et al—"Catalyst free 1,3-dipolar cycloaddition of 3-oxo-1,2-pyrazolidinium ylides to β-trifluoroacetyl vinyl ethyl ether: Synthesis of 6-trifluoroacetyl substituted bicyclic pyrazolidinoes", Journal of Fluorine Chemistry (2011) vol. 132, pp. 402-408, 7 pgs.

Sauzem, P. D. et al.—"Design and microwave-assisted synthesis of 5-trifluoromethyl-4, 5-dihydro-$H$-pyrazoles: Novel agents with analgesic and anti-inflammatory properties", European Journal of Medicinal Chemistry, (2008) vol. 43, pp. 1237-1247, 11 pgs.

U.S. Appl. No. 12/999,673, filed Dec. 17, 2010, Braun, et al.
U.S. Appl. No. 13/120,505, filed Mar. 23, 2011, Braun, et al.
U.S. Appl. No. 12/999,714, filed Mar. 31, 2011, Braun, et al.
U.S. Appl. No. 12/999,730, filed May 23, 2011, Braun, et al.
U.S. Appl. No. 12/999,750, filed Apr. 7, 2011, Braun, et al.

PROCESS FOR CHEMICAL SYNTHESIS FROM AN ALKENONE MADE FROM A HALOGENATED PRECURSOR

CROSS-REFERENCE TO RELATED APPLICATIONS

This application is a continuation-in-part application which claims priority benefit to U.S. application Ser. No. 12/999,730 which is the U.S. national stage entry under 35 U.S.C. §371 of International Application No. PCT/EP2010/059549 filed on Jul. 5, 2010, which claims priority under 35U.S.C. §119(a)-(d) or (f), §365(b) or §365(a) to International Application No. PCT/EP2009/058525 filed on Jul. 6, 2009 and to European Application No. EP 10150229.2 filed on Jan. 7, 2010, the whole content of each of these applications being incorporated herein by reference for all purposes.

TECHNICAL FIELD OF THE INVENTION

The present invention relates to a process for chemical synthesis from an alkenone made from a halogenated precursor, in particular a process for the synthesis of an agriculturally active or pharmaceutically active compound.

BACKGROUND OF THE INVENTION

Halogenated alkenones, such as 4-ethoxy-1,1,1-trifluoro-3-butenone (ETFBO), are building blocks in chemical synthesis, as disclosed, for example, in U.S. Pat. No. 5,708,175, incorporated herein by reference. These alkenones may be prepared by reacting an acid chloride with a vinyl ether in the presence of a base, as described in the aforementioned U.S. patent. For this reaction, the base may also be used in excess as a solvent.

WO 03/066558, incorporated herein by reference, discloses production of alkenones from vinyl ethers and acid halides or acid anhydrides in the presence of onium salts. In the case of trifluoroacetic anhydride addition to ethyl vinyl ether, both addition of ethyl vinyl ether to a reaction medium containing trifluoroacetic anhydride and addition of trifluoroacetic anhydride to a reaction medium containing ethyl vinyl ether are described.

WO 2004/108647, incorporated herein by reference, discloses a simplified production of alkenones comprising addition of carboxylic acid halides to vinyl ethers. In the examples, trifluoroacetyl chloride is added to ethyl vinyl ether.

SUMMARY OF THE INVENTION

It is an object of the present invention to provide an improved process for chemicals synthesis which includes the preparation of a halogenated precursor of an alkenone.

It is another object of the present invention to provide a process for chemicals synthesis which includes the manufacture of an alkenone from an halogenated precursor, in particular concerning the selectivity and the yield of the production, whereby, amongst others, separation of the alkenone product can be simplified and loss of material and need for disposal of by-products can be reduced.

It is yet another object of the present invention to provide a process for synthesizing a chemical, which includes three steps:
a first step for preparing a halogenated precursor of an alkenone, which comprises reacting a carboxylic acid halide with a vinyl ether;
a second step for preparing an alkenone, which comprises eliminating hydrogen halide from such alkenone precursor to form the alkenone; and
a third step for synthesizing a chemical, which comprises using the alkenone as a building block to synthesize the chemical.

A first aspect of the present invention relate to a process for synthesizing a chemical, comprising the following steps:
carrying out a first step to prepare a halogenated precursor of an alkenone, said first step comprising at least one step selected from the group consisting of:
(a) reacting a carboxylic acid halide with a vinyl ether in a liquid reaction medium to prepare said halogenated precursor of an alkenone, wherein at least a part of said carboxylic acid halide is introduced in liquid state into said reaction medium, wherein said reaction is carried out under conditions of pressure and temperature under which said carboxylic acid halide is gaseous, and wherein, when the liquid carboxylic acid halide gets into the gaseous state in the liquid reaction medium, gas bubbles are generated in the liquid reaction medium to provide the reaction medium in turbulent state; and
(a') reacting a carboxylic acid halide with a vinyl ether in a liquid reaction medium comprising an alkenone or a halogenated precursor of an alkenone;
(b) eliminating hydrogen halide from said halogenated precursor of the alkenone formed in the first step to form the alkenone; and
(c) using said alkenone as a building block to synthesize said chemical.

An embodiment of the first aspect of the present invention relate to a process for synthesizing a chemical, comprising the following steps:
(a) reacting a carboxylic acid halide with a vinyl ether in a liquid reaction medium to prepare a halogenated precursor of an alkenone, wherein at least a part of said carboxylic acid halide is introduced in liquid state into said reaction medium, wherein said reaction is carried out under conditions of pressure and temperature under which said carboxylic acid halide is gaseous, and wherein, when the liquid carboxylic acid halide gets into the gaseous state in the liquid reaction medium, gas bubbles are generated in the liquid reaction medium to provide the reaction medium in turbulent state;
(b) eliminating hydrogen halide from said halogenated precursor of the alkenone to form the alkenone; and
(c) using said alkenone as a building block to synthesize said chemical.

Another embodiment of the first aspect of the present invention relate to a process for synthesizing a chemical, comprising the following steps:
a') reacting a carboxylic acid halide with a vinyl ether in a liquid reaction medium comprising an alkenone or a halogenated precursor of the alkenone;
b) eliminating hydrogen halide from a halogenated precursor of an alkenone obtained in step (a') to form an alkenone; and
c) using said alkenone obtained from step (b) as a building block to synthesize said chemical.

A second aspect of the present invention relate to a process for synthesizing a chemical, comprising the following steps:
a") preparing a halogenated precursor of an alkenone, said halogenated precursor corresponding to Formula (I): $R^1$—C(O)—$CH_2$—CH(X)—$OR^2$ (I), wherein X is fluorine, chlorine, or bromine; $R^1$ represents a C1-C10 alkyl group which is optionally substituted by at least one halogen atom (preferably $R^1$ represents $CF_3$, $CF_2Cl$, $CF_2H$, $C_2F_5$, or $C_3F_7$) or represents CF3C(O)CH2; and $R^2$ represents aryl, substituted aryl, or a C1-C10 alkyl group which is optionally substituted by at least one halogen atom, said step (a") comprising reacting an acid halide corresponding to Formula (II): $R^1$—C(O)X (II) in which X and $R^1$ has the same meaning as in Formula (I), with a vinyl ether corresponding to Formula (III): CH2=C(H)—$OR^2$ (III) in which $R^2$ has the same meaning as in Formula (I), to form said halogenated precursor;

b') eliminating hydrogen halide from said halogenated precursor obtained in step (a") to form an alkenone, wherein said hydrogen halide elimination comprises at least one thermolysis treatment selected from the group consisting of a flash thermolysis, vacuum thermolysis, and thermolysis under stripping with inert gas; and c) using said alkenone as a building block to synthesize said chemical.

A third aspect of the present invention relate to a process for synthesizing a chemical, comprising the following steps:

a") preparing a halogenated precursor of an alkenone, said halogenated precursor corresponding to Formula (I): $R^1$—C(O)—CH2-CH(X)—$OR^2$ (I), wherein X is fluorine, chlorine, or bromine; wherein $R^1$ represents a C1-C10 alkyl group which is optionally substituted by at least one halogen atom (preferably $R^1$ represents $CF_3$, $CF_2Cl$, $CF_2H$, $C_2F_5$, or $C_3F_7$) or $R^1$ represents CF3C(O)CH2; and $R^2$ represents aryl, substituted aryl, or a C1-C10 alkyl group which is optionally substituted by at least one halogen atom, said step (a") comprising reacting an acid halide corresponding to Formula (II): $R^1$—C(O)X (II) in which X and $R^1$ has the same meaning as in Formula (I), with a vinyl ether corresponding to Formula (III): CH2=C(H)—$OR^2$ (III) in which $R^2$ has the same meaning as in Formula (I), to form said halogenated precursor;

b") eliminating hydrogen halide from said halogenated precursor obtained in step (a") to form an alkenone, wherein said hydrogen halide elimination comprises a thermolysis treatment carried out at a temperature from greater than 90° C. to 120° C.; and c) using said alkenone as a building block to synthesize said chemical.

According to any or all of the aspects and embodiments disclosed herein, the synthesized chemical is preferably an agriculturally active compound or a pharmaceutically active compound. Step (c) preferably comprises converting said alkenone obtained in the second step (such as step (b), step (b') and/or step (b")) into said agriculturally active or pharmaceutically active compound.

DETAILED DESCRIPTION OF THE PREFERRED EMBODIMENTS

According to an embodiment, the first step for preparing a halogenated alkenone precursor may comprise:

(a") preparing a halogenated alkenone precursor of formula (I)

$R^1$—C(O)—CH2—CHX—$OR^2$ (I)

wherein $R^1$ represents a C1-C10 alkyl group which is optionally substituted by at least one halogen atom (preferably $R^1$ represents $CF_3$, $CF_2Cl$, $CF_2H$, $C_2F_5$, or $C_3F_7$) or $R^1$ represents CF3C(O)CH2; wherein $R^2$ represents aryl, substituted aryl, or a C1-C10 alkyl group which is optionally substituted by at least one halogen atom; and wherein X represents fluorine, chlorine, or bromine.

In said step (a"), an acid halide corresponding to Formula (II): $R^1$—C(O)X (II) in which X and $R^1$ has the same meaning as in Formula (I), is reacted with a vinyl ether corresponding to Formula (III): $CH_2$=C(H)—$OR^2$ (III) in which $R^2$ has the same meaning as in Formula (I), to form the halogenated precursor of Formula (I).

$R^1$ is often a fluorinated C1-C4 alkyl group. $R^1$ preferably represents methyl, ethyl, n-propyl, isopropyl, methyl substituted by at least one fluorine atom, ethyl substituted by at least one fluorine atom, n-propyl substituted by at least one fluorine atom, or isopropyl substituted by at least one fluorine atom. It is especially preferred if $R^1$ represents methyl, ethyl, methyl substituted by at least one fluorine atom, or ethyl substituted by at least one fluorine atom. $CF_3$, $CF_2H$, $CF_2Cl$, $C_2F_5$, $C_3F_7$ are particularly preferred as $R^1$. $CF_3$, $CF_2Cl$, and $CF_2H$ are more particularly preferred as $R^1$.

$R^2$ can be selected for example from aryl, for example, phenyl, C1-C4 alkyl groups and/or phenyl substituted by halogen atoms. $R^2$ is often a C1-C4 alkyl group. Preferably, $R^2$ represents a linear C1-C4 alkyl group or branched C3-C4 alkyl group. More preferably, $R^2$ represents methyl, ethyl, n-propyl, or isopropyl. Most preferably, $R^2$ represents a methyl group or an ethyl group.

In step (a"), preferred $R^1$ is a fluorinated C1-C4 alkyl group and preferred $R^2$ is a C1-C4 alkyl group.

X is preferably selected from the group consisting of fluorine and chlorine, more preferably X is chlorine.

The preferred starting materials for this first step described above correspond to the preferred starting materials for the process according to the present invention.

An acyl chloride of formula (II): $R^1$—C(O)X wherein $R^1$ is preferably a fluorinated C1-C4 alkyl group.

An acyl chloride of formula (II): $R^1$—C(O)X wherein $R^1$ is more preferably $CF_3$, $CF_2H$, $CF_2Cl$, $C_2F_5$, or $C_3F_7$.

Most preferably, the carboxylic acid halide used in the first step is trifluoroacetyl chloride.

A vinyl ether of formula (II): $CH_2$=C(H)—$OR^2$ wherein $R^2$ is preferably a C1-C4 alkyl group.

A vinyl ether of formula (II): $CH_2$=C(H)—$OR^2$ wherein $R^2$ is more preferably methyl, ethyl, n-propyl, or isopropyl.

The preferred halogenated precursor of an alkenone made by the first process step is 4-Chloro-4-Ethoxy-1,1,1-trifluoro-3-butan-2-one (CETFBO).

The alkenone which may be prepared from the halogenated alkenone precursor of formula (I) via the second step of the process according to the present invention is preferably an alkenone of formula (IV),

$R^1$—C(O)—CH=CH—$OR^2$ (IV), wherein $R^1$ and $R^2$ have the same meaning as in formula (I).

According to another embodiment, the first step for preparing a halogenated precursor of an alkenone in the process according to the present invention may comprise:

reacting a carboxylic acid halide with a vinyl ether in a liquid reaction medium in turbulent state.

For this embodiment of the first process step, the term "turbulent state" in the first process step includes the meaning used in fluid dynamics, indicating high momentum convection and high Reynolds numbers, as distinguished from a "laminar" state; but the term is not limited to this meaning. The term "turbulent" broadly denotes a very efficient mixing of the reaction mixture.

The turbulent state of the reaction medium can be achieved, for example, by an operation selected from the group consisting of stirring, passing the reaction medium through a flow resistance, and mixing the reaction medium through introduction of gas bubbles (such as for example inert gas bubbles or starting material gas bubbles).

In a preferred aspect, the reaction is carried out under conditions of pressure and temperature under which at least one of the starting materials is gaseous. In that case, it is advantageous to introduce the starting material in liquid form. Gas bubbles are generated which provide turbulence in the reaction medium when the liquefied starting material gets into the gaseous state. Further, the vaporization consumes heat from the reaction medium what is also very advantageous. Carboxylic acid halide, in particular trifluoroacetyl chloride is a suitable starting material for this purpose.

Accordingly, the first process step for the manufacture of a halogenated precursor of an alkenone may comprise:

reacting a carboxylic acid halide with a vinyl ether in a liquid reaction medium, wherein at least a part of the carboxylic acid halide is introduced into the reaction medium in liquid state.

Preferably, at least 99% by weight of the acyl halide is introduced into the reaction medium in liquid state.

A particular embodiment of the first process step may comprise:

(a) reacting a carboxylic acid halide with a vinyl ether in a liquid reaction medium to prepare a halogenated precursor of an alkenone, wherein at least a part of said carboxylic acid halide is introduced in liquid state into said reaction medium, wherein said reaction is carried out under conditions of pressure and temperature under which said carboxylic acid halide is gaseous, and wherein, when the liquid carboxylic acid halide gets into the gaseous state in the liquid reaction medium, gas bubbles are generated in the liquid reaction medium to provide the reaction medium in turbulent state.

In such embodiment, the turbulent state in the liquid reaction medium may be further achieved by an operation selected from the group consisting of stirring and passing the reaction medium through a flow resistance. The stirring in the reaction medium may be realized by means of internal stirring such as a turbine or an agitator, or by means of a recirculation pipe exterior to the reactor.

Typical examples of a flow resistance are for example shaped bodies which can be placed in a reactor such as glass rings and Raschig rings.

In a particular aspect of the first process step, which is particularly advantageous when the first process step is carried out in continuous mode, the vinyl ether and the carboxylic acid halide may be introduced into the liquid reaction medium through a concentric nozzle having an internal supply tube and an external supply tube. In this aspect, the vinyl ether is preferably supplied through the internal supply tube and the carboxylic acid halide is preferably supplied through the external supply tube.

It has been found, surprisingly, that by creating a turbulent state in the liquid reaction medium, hot spots can be substantially avoided in said reaction medium, thereby improving the yield and purity of the halogenated precursor of the alkenone in the first process step and of the alkenone obtained from the precursor in a subsequent (second) process step.

For the purpose of the present invention, the term "hot spot" denotes in particular a zone of the reaction medium having a substantially higher temperature than the temperature at which the reaction is carried out. "Substantially higher temperature" is understood a temperature which is at least 5° C., often at least 10° C. higher than the average temperature of the liquid reaction medium.

It was observed that hot spots cause the elimination of hydrogen halide, and hydrogen halide was found to cause undesired side reactions. Thus, according to some embodiments of the present invention, it is preferred to provide a very low level of hydrogen halide formation in the addition reaction in the first process step, preferably to substantially avoid hydrogen halide formation at all. "Substantially avoid" denotes in particular maintaining a content of hydrogen halide in the reaction medium of equal to or lower than 1% wt. Preferably, this hydrogen halide content is maintained equal to or lower than 0.5% wt. When the formation of hydrogen halide is substantially avoided, a content of hydrogen halide in the reaction medium equal to or higher than 0.01% wt albeit equal to or higher than 0.1% wt relative to the total weight of the reaction medium is acceptable.

The first process step generally comprises carrying out the reaction at a temperature from 0° C. to 40° C., preferably from 10° C. to 30° C., more preferably at equal to or about 25° C. and most preferably at equal to or about 20° C. If desired, the reaction in the first process step can also be performed at temperatures below 0° C.; e.g., between 0° C. and −50° C., but the reaction rate is lower. It is preferred to operate the first process step at a temperature from 0° C. to 40° C.

In the first process step according to this specific embodiment, the reaction is preferably carried out in a continuously stirred tank reactor (CSTR).

In a particular aspect, the continuously stirred tank reactor may be combined with a plug flow reactor. In that case, generally, at least a part of the liquid reaction medium is withdrawn from the continuously stirred tank reactor and subjected to further reaction in a plug flow reactor. In this case, the CSTR reactor is usually in the turbulent state while the plug-flow reactor can be in turbulent or laminar flow state. In a plug-flow reactor, it is preferred to perform the reaction in a laminar flow state if the acyl halide is reacted with the vinyl ether in a molar ratio of acyl halide:vinyl ether of 1:1 or lower than 1:1 (i.e., in the presence of equimolar amounts or with an excess of the vinyl ether). If the plug flow reactor is operated in a turbulent state, it is preferred to apply an excess of the acyl halide because the gas bubbles of the acyl halide intensify the mixing of the components of the reaction medium.

Particular embodiments of CSTR include reactors which consist of one or more cylindrical or spherical tanks wherein the turbulent state of the liquid reaction medium is created by any of the means described above. When more than one CSTR reactor is used, for example 2, 3 or 4 reactors, it is advantageous to split the feed of vinyl ether so as to feed vinyl ether to each reactor.

Particular embodiments of plug flow reactor are in the form of a cylindrical tube through which the feed enters at one end and exits at the other end.

The addition reaction of the acid halide and the vinyl ether in the first process step is exothermic. As mentioned above, it is preferably performed at a temperature from 0° C. to 40° C., and thus, the reaction medium is preferably cooled.

In another particular aspect, the continuously stirred tank reactor is combined with a heat exchanger. Said heat exchanger advantageously can remove heat from the reactor during the exothermic reaction. The heat exchanger can be a separated device added to the CSTR or the heat exchanger and the reactor can be combined into a single piece of equipment.

By way of illustration, the following devices can be used as heat exchangers, especially when added to the CSTR: double jacket, external and internal coils etc.

If the heat exchanger is a device separated from the reactor, a part of the reaction medium can be passed through a loop via a heat exchanger or a cooling machine. This is preferably performed continuously.

The stirrers may be single-stage or multistage embodiments, especially those which produce not only a tangential flow component but also an axial flow field. Preferred stirrers are those having 1 to 7 stirring blade stages attached, preferably equidistantly, on the axial stirrer shaft. Examples are blade, anchor, impeller, Pfaudler, disk, helical, bar, finger propeller, sigma, paddle, pitched-blade and coaxial stirrers, such as cross-arm, multiflow, multipulse countercurrent, Intermig and Interpro stirrers. A suitable reactor is described in U.S. Pat. No. 6,428,199, incorporated herein by reference. The reactor described therein has a stirring mechanism, incoming and outgoing lines and a removable head wherein both the incoming and outgoing lines and the stirring mechanism are installed on the reactor floor.

A reactor which can be used in the first process step of the present invention is described in US2006/198771, incorporated herein by reference. A cylindrical vertical stirred reactor provided with means of injection of gaseous (or liquid) reactants at the bottom, and, as essential parts, centrifugal turbines arranged along a single vertical agitating shaft. The shaft is driven by a geared motor unit which is most often situated either above or below the reactor. The reactor may be equipped with counterbaffles and/or a heat exchanger.

Another apparatus which can be used for preparing a halogenated precursor of an alkenone in the first process step is now described.

The apparatus comprises two means, wherein the first means comprises a circulation system with a boiler, pipes filled with Raschig rings, centrifugal pump, tubular reactors each with a pipe. Product can be added or removed (for analysis purposes) before and after each of these reactors. For safety reasons, a further length of pipe with cooler and cold traps can be mounted after circulation; wherein the second means is used as a receiver and for the thermolysis of the organic product precursors to the organic products in the subsequent second process step, for example, from 4-chloro-4-ethoxy-1,1,1-trifluoro-butan-2-one (CETFBO) to 4-ethoxy-1,1,1-trifluoro-butan-2-one (ETFBO) and comprises ceramic boiler with column pipes with Raschig rings and cooler with take-off.

Reactors which are coated with a ceramic at least on the inner walls are especially suitable because ceramic was found to be very resistant under the aggressive conditions of the first step of the process according to the present invention.

According to yet another embodiment of the process according to the present invention, the first process step for the manufacture of a halogenated precursor of an alkenone may comprise:
reacting a carboxylic acid halide with a vinyl ether in a liquid reaction medium, wherein the reaction is performed in a reactor the inner walls of which are coated with a ceramic.

If desired, the reactor walls may consist of a ceramic. It is preferred that at least those parts of the reactor which are in contact with the reaction medium are coated with ceramic.

The preferred starting materials of this embodiment of the first process step correspond to the preferred starting materials of the embodiment described above in reference to step (a"). An acyl chloride of formula (II): $R^1$—C(O)X wherein $R^1$ is preferably $CF_3$, $CF_2H$, $CF_2Cl$, $C_2F_5$, or $C_3F_7$. A vinyl ether of formula (III): $CH_2$=C(H)—$OR^2$ wherein $R^2$ preferably represents methyl, ethyl, n-propyl, or isopropyl. The preferred alkenone precursor made in the first step is 4-chloro-4-ethoxy-1,1,1-trifluoro-butan-2-one (CETFBO).

According to an embodiment, the first process step for preparing the halogenated precursor of an alkenone may comprise:
a') reacting a carboxylic acid halide with a vinyl ether in a liquid reaction medium comprising an alkenone or a halogenated precursor of the alkenone.

It has been found that alkenones, in particular ETFBO, and halogenated precursors, in particular CETFBO (1,1,1-trifluoro-4-chloro-4-ethoxybutan-2-one) can be advantageously used as solvent for the reaction of the carboxylic acid halide with the vinyl ether in the first step of the process according to the present invention. The halogenated precursor and alkenone used as a solvent may correspond to the halogenated precursor and its dehydrohalogenated alkenone, respectively.

In a preferred embodiment, the halogenated precursor of the alkenone which is present in the reaction medium corresponds to the halogenated alkenone precursor which is prepared in the first step of the process.

The halogenated precursor of the alkenone which may be present in the reaction medium in step (a') may be of formula (I)

$$R^1\text{—C(O)—CH}_2\text{—CHX—OR}^2 \quad \text{(I)}$$

wherein $R^1$ represents a C1-C10 alkyl group which is optionally substituted by at least one halogen atom (preferably $R^1$ represents $CF_3$, $CF_2Cl$, $CF_2H$, $C_2F_5$, or $C_3F_7$) or $R^1$ represents CF3C(O)CH2; wherein $R^2$ represents aryl, substituted aryl, or a C1-C10 alkyl group which is optionally substituted by at least one halogen atom (preferably $R^2$ represents methyl, ethyl, n-propyl, or isopropyl); and wherein X represents fluorine, chlorine, or bromine.

In another preferred embodiment, the alkenone which is present in the reaction medium corresponds to the alkenone which is prepared in the second step of the process.

The alkenone which may be present in the reaction medium in step (a') may be of formula (IV),

$$R^1\text{—C(O)—CH=CH—OR}^2 \quad \text{(IV)}$$

wherein $R^1$ and $R^2$ have the same meaning as in formula (I).

In particular, according to this embodiment of the first process step, the liquid reaction medium for said reaction comprises an alkenone, in particular ETFBO, as a solvent. The alkenone is generally used in an amount of from 50 to 99% by weight, preferably from 60 to 99% by weight, more preferably from 75 to 99% by weight of the alkenone relative to the total weight of the reaction medium.

This embodiment is particularly advantageous for starting up the reaction in the first process step.

The alkenone-containing liquid reaction medium preferably comprises additional alkenone which is provided to the reaction from an external source, for example an earlier batch manufacture of alkenone. In one aspect of this embodiment, the reaction in the first process step is carried out by introducing carboxylic acid halide into said alkenone containing liquid reaction medium, in particular during start-up of the manufacturing process. The formation of the halogenated precursor of the alkenone after introduction of vinyl ether into the liquid reaction medium comprising the alkenone and the carboxylic acid halide will generally provide a liquid reaction medium containing the halogenated precursor and the alkenone.

It is understood that this embodiment may also be applied for reaction of the same type as reaction described above wherein the vinyl ether is not added to a reaction medium containing carboxylic acid halide. For example, vinyl ether may be dissolved in the alkenone-containing reaction medium and then, carboxylic acid halide is added to the reaction medium containing vinyl ether and alkenone.

In another embodiment of the first process step, the liquid reaction medium for the reaction of the carboxylic acid halide with the vinyl ether comprises a halogenated precursor of the alkenone, in particular CETFBO. The halogenated precursor is generally used in an amount of from 50 to 99% by weight, preferably from 60 to 99% by weight, more preferably from 75 to 99% by weight of the halogenated precursor of the alkenone to the total weight of the reaction medium.

In a preferred embodiment, the first process step is carried out in continuous mode. In a continuous process, the content of the halogenated precursor of the alkenone in the liquid reaction medium is generally kept in a range from 50 to 99%, preferably in a range from 60 to 99%, more preferably in a range from 75 to 99% by weight of halogenated precursor relative to the total weight of the reaction medium. This is particularly advantageous for a continuous process operated in steady-state, for example in a continuously stirred tank reactor (CSTR).

In a preferred embodiment of this aspect, the remainder of the liquid reaction medium comprises carboxylic acid halide.

For the first process step, the liquid reaction medium generally contains at least 0.5% by weight, preferably at least 1% by weight of carboxylic acid halide relative to the total weight of the reaction medium. Preferably this content is at least 5% weight. The liquid generally contains less than about 20% by weight of carboxylic acid halide relative to the total weight of the reaction medium. Preferably this content is less than 10% weight. Preferably, the liquid reaction medium contains from 5 to 10% by weight of carboxylic acid halide relative to the total weight of the reaction medium. This particular embodiment may also be applied to the various aspects of the first step in the process according to the invention described herein.

The reaction in the first process step may be carried out in the presence of an additional solvent. The term "additional solvent" is understood to denote a solvent different from the reactants used in the first step, the products of said reaction made in the first step, and the additional alkenone or precursor of the alkenone. The additional solvent to be used may, for example, be an aromatic hydrocarbon such as benzene, toluene or xylene, an aliphatic hydrocarbon such as pentane or hexane; a halogenated hydrocarbon such as methylene chloride, chloroform or ethylene dichloride or fluorinated hydrocarbons such as 1,1,1,3,3-pentafluorobutane (commercialized by Solvay Fluor GmbH under the trademark Solkane® 365mfc); or an ether such as diethyl ether, dibutyl ether or tetrahydrofuran. Among these solvent choices, an aromatic hydrocarbon is preferred. Particularly preferred among these solvents is benzene or toluene. These solvents may be used alone or in combination as a mixture. If appropriate, the additional solvent is used usually in an amount of from 1 to 35 parts by weight, preferably from 3 to 16 parts by weight, per part by weight of the carboxylic acid halide. It is however preferred to carry out the reaction in the first process step in the substantial absence or absence of an additional solvent.

In a particular embodiment of the first process step, the solvent used in the reaction medium may further comprise at least one haloether, for example a chloroether such as chloroalkyl-alkyl ethers, in particular chloroethyl-ethyl ether. In this case, the content of the haloether in the liquid reaction medium is generally from 0.1 to 5%, often from 0.5 to 2%, by weight relative to the total weight of the liquid reaction medium. It has been found that haloethers are suitable solvents which can be incorporated in the liquid reaction medium, in particular in the indicated concentration ranges while achieving high productivity and selectivity to the halogenated precursor of alkenone. In a continuous process, the content of haloether is preferably maintained in the concentration range indicated here above.

It is more particularly preferred to carry out, in the first process step, the reaction in a liquid reaction medium consisting or consisting essentially of the alkenone, the halogenated precursor of alkenone, the carboxylic acid halide, and the vinyl ether. This embodiment has particular advantages for a subsequent process step such as for example a thermolysis or purification operations.

In the first process step according to the present invention and in its particular aspects and embodiments described herein, the molar ratio of the acid halide to vinyl ether preferably is from 0.8 to 1.2, and particularly preferably from 0.8:1 to about 1. Most preferably, the molar ratio of the acid halide to vinyl ether is about 1.

In the first step of the process according to the present invention and in any of its particular aspects and embodiments described herein, the vinyl ether is generally introduced into the liquid reaction medium at a rate of from 0.01 to 2 mol/hour/mol of carboxylic acid halide. Preferably this rate is from 0.5 to 1.5 mol/hour/mol of carboxylic acid halide. A rate of about 1 mol/hour/mol of carboxylic acid halide has given good results.

The first step of the process according to the invention and any of its particular aspects and embodiments described herein can be carried out batchwise or continuously In the first step of the process according to the present invention and in any of its particular aspects and embodiments described herein, it is especially beneficial, in particular in a continuous process to control the concentration of the vinyl ether in the liquid reaction medium. Generally, this concentration is less than 5% by weight relative to the total weight of the liquid reaction medium. Often the concentration of the vinyl ether in the liquid reaction medium is equal to less than 1% by weight relative to the total weight of the liquid reaction medium. Preferably, this concentration is equal to less than 0.5% by weight relative to the total weight of the liquid reaction medium. Generally, this concentration is at least 0.1% by weight relative to the total weight of the liquid reaction medium.

It has been found that controlling the concentration of the vinyl ether allows to avoid or control the formation of byproducts such as chloroethers or polymeric materials and improves the yield and purity of the alkenone which can be manufactured from the alkenone precursor produced according to the second step of the process in accordance to the present invention.

The present invention concerns in consequence also another aspect of the first process step for the manufacture of a halogenated precursor of an alkenone, for example as disclosed thereabove, which comprises:

reacting a carboxylic acid halide continuously with a vinyl ether in a liquid reaction medium, wherein the concentration of the vinyl ether in the liquid reaction medium is controlled and preferably maintained in the ranges disclosed here before.

It has been found that use of the halogenated precursor of the alkenone and, preferably, the alkenone as solvents avoids particularly the formation of other unwanted compounds and improves the yield and purity of the organic products, in particular the halogenated precursor of the alkenone and, preferably, the alkenone. That is, use of the halogenated precursor of the alkenone (formed in the first step) and, preferably, the alkenone (formed in the second step) as solvents avoids complex post-treatments, for example, distillation of solvents, purification of the by-products caused by solvents etc.

In one embodiment of the process according to the present invention, the halogenated precursor of the alkenone which is obtained in the first step of the process according to the present invention can be used as such. For example, the halogenated precursor of the alkenone formed in the first step can be used as solvent, e.g., as solvent in a subsequently-performed step (e.g., second step) according to the present invention.

In another aspect of the process according to the present invention, the halogenated precursor of the alkenone which is obtained in the first step of the process according to the present invention is dehydrohalogenated by the elimination of hydrogen halide to form the respective alkenone.

Consequently, the process according to the present invention further comprises a second step for preparing an alkenone, which comprises (b) eliminating hydrogen halide from said halogenated precursor of the alkenone to form the alkenone.

The halogenated precursor of the alkenone is formed in the first step of the process, for example, in any of the various particular aspects and embodiments of the first step described herein. Said first step preferably comprises a step selected from the group consisting of step (a), step (a') and step (a") described herein.

According to one embodiment of the present process, the elimination of hydrogen halide in the second step is carried out simultaneously during the first step carried out for the formation of the halogenated precursor of the alkenone. For example, the elimination of hydrogen halide may be carried out simultaneously during the formation of the halogenated precursor of the alkenone in the presence of an acid scavenger and/or by thermally inducing the elimination of hydrogen halide. The acid scavenger (a base) to be used may, for example, be a nitrogen-containing heterocyclic compound such as pyridine, quinoline or picoline; or a tertiary base such as triethylamine, dimethylaniline, diethylaniline or 4-dimethylaminopyridine. Among them, pyridine, triethylamine, dimethylaniline, diethylaniline or 4-dimethylaminopyridine is preferred. Among them, pyridine is particularly preferred.

These acid scavengers (or bases) may be used alone or in combination as a mixture. If appropriate, the acid scavenger may be used in an amount of less than 1 equivalent, preferably less than 0.8 equivalents per mol carboxylic acid halide. In alternate embodiments if appropriate, the base may be used usually in an amount of from 1.0 to 3.0 equivalents, preferably from 1.05 to 1.5 equivalents, per mol carboxylic acid halide. If, instead or additionally to the presence of a base, a thermal elimination of hydrogen halide is intended to be carried out, then the temperature of the reaction mixture is preferably equal to or higher than 50° C. The temperature of the reaction mixture is preferably equal to or lower than 100° C.

If desired, an additional solvent may be present during the elimination of hydrogen halide in the second process step. The term "additional solvent" has the same meaning as defined above in the context of the first process step.

In a first particular embodiment of the present process, the carboxylic acid halide is trifluoroacetyl chloride. Preferably, the trifluoroacetyl chloride is fed in liquid state into the reaction medium.

In a second particular embodiment of the present process, the carboxylic acid halide is chlorodifluoroacetyl chloride.

In a third particular embodiment of the present process, the carboxylic acid halide is Difluoroacetyl chloride.

In a fourth particular embodiment of the present process, the carboxylic acid halide is trifluoroacetyl fluoride.

In a fifth particular embodiment of the present process, the carboxylic acid halide is (trifluoroaceto)acetyl fluoride.

In a sixth particular embodiment of the present process, which is preferred, the process for the preparation of a halogenated precursor of an alkenone and the elimination of hydrogen halide is carried out in the substantial or complete absence of an acid scavenger especially when a carboxylic acid chloride as described herein before is used.

In a seventh particular embodiment of the present process, which is preferred, the preparation of the halogenated precursor of the alkenone and the elimination of hydrogen halide is carried out in the substantial or complete absence of additional solvent.

In a eighth particular embodiment of the present process, which is preferred, the preparation of the halogenated precursor of the alkenone and the elimination of hydrogen halide is preferably carried out in the substantial or complete absence of an acid scavenger and of additional solvent, as described here before. The sixth to eighth, in particular the eighth particular embodiment can be advantageously combined with any of the first to fifth particular embodiment.

In the sixth to eighth particular embodiments of the present process according to the present invention, "Substantial absence" typically denotes an optional content of equal to or less than 1% by weight, more particularly equal to or less than 0.5% by weight of acid scavenger and/or solvent relative to the total weight of the reaction medium. "Complete absence" in this context typically denotes a process wherein no voluntary addition of acid scavenger and/or solvent to the reaction medium has been carried out. Typically "complete absence" means that no acid scavenger and/or solvent can be detected in a GC of the reaction medium.

In particular the sixth to eighth particular embodiments of the process according to the invention allow for particularly efficient isolation of, if desired, the halogenated precursor of the alkenone and in particular the desired alkenone as reaction proceeds selectively and separation is facilitated by the limitation albeit substantial absence of components different from the starting material and the products of the reaction.

As mentioned above, a preferred embodiment of the invention concerns a process for preparing an alkenone, which comprises:

(a') reacting a carboxylic acid halide with a vinyl ether in a liquid reaction medium containing an alkenone or a halogenated precursor thereof, and (b) eliminating hydrogen halide from a halogenated precursor of an alkenone obtained in step (a') to form an alkenone.

This embodiment of the process according to the invention, and the particular aspects thereof, generally comprises carrying out the reaction of the first step (such as step (a), step (a') and/or step (a")) at a first temperature and carrying out the second step (such as step (b), step (b') and/or step (b")) at a second temperature higher than the first temperature.

The first temperature is generally less than 50° C., often less than 40° C., preferably equal to or less than 30° C. In one aspect, the temperature is preferably equal to or less than about −25° C. The first temperature is generally at least −50° C., often equal to or greater than −40° C., preferably equal to or greater than −30° C.

The second temperature is generally at least 50° C., often equal to or greater than 60° C., preferably equal to or greater than 70° C. The second temperature is generally less than 150° C., often less than 100° C., preferably equal to or less than about 80° C.

The process according to the invention, and any of the particular embodiments and aspects thereof, generally comprises carrying out the reaction in the first step (such as step (a), (a') and/or (a")) at a first pressure and carrying out the second step (such as step (b), step (b') and/or (b")) at a second pressure lower than the first pressure.

The first pressure is generally chosen to maintain the reaction medium in the liquid state. For example, if trifluoroacetyl chloride is used as acid halide, the first pressure is advantageously atmospheric pressure at a reaction temperature of equal to or less than about −25° C. The first pressure is advantageously a pressure equal to or greater than about 4, preferably about 5 bar abs to equal to or less than about 10 bar at a reaction temperature of from 20 to 30° C.

The second pressure is preferably chosen to allow for fractional distillation at least of the alkenone from the reaction medium. A typical second pressure is from 1 to about $10^{-3}$ bar abs.

In one embodiment of the process according to the invention and the particular aspects and embodiments thereof, which is advantageous when the process is carried out batch-wise, the first step (such as step (a), step (a') and/or step (a")) and the second step (such as step (b), step (b') and/or step (b")) are carried out in the same reaction zone, for example, a vessel surmounted by a distillation column.

In another embodiment of the process according to the invention, and any of the particular aspects and embodiments thereof, which is advantageous when the process is carried out batch-wise or continuously, the first step (such as step (a), step (a') and/or step (a")) is carried out in a first reaction zone, and the second step (such as step (b), step (b') and/or step (b")) is carried out in a second reaction zone different from the first reaction zone.

The first reaction zone is often an optionally stirred tank reactor, preferably a continuously stirred tank reactor. The second reaction zone can be, for example, a distillation column.

In an ninth particular embodiment of the process according to the invention, which is preferred, the process further comprises separating the alkenone produced in the second step (such as step (b), step (b') and/or (b")) from hydrogen halide, unreacted carboxylic acid halide, and unreacted halogenated precursor (and some traces of polymeric material); and optionally recycling carboxylic acid halide to the first step (such as step (a), step (a'), step (a") or combinations thereof)) and the halogenated precursor to the second step (such as step (b), step (b'), step (b") or combinations thereof).

A distillation, in particular a fractional distillation, is preferred as separation technique to separate the alkenone, in particular from the reaction mixture of the second step. Preferably, a part of the reaction medium is removed from the reactor of the first step, carried in a loop and returned to the reactor of the first step. In such a loop, it is possible to cool the circulated part of the reaction medium. This serves to keep the temperature of the reaction mixture in a desired range. Further, as will be described below, circulating continuously a part of the reaction mixture improves the mixing of the reaction medium; the resulting turbulent state of the reaction medium helps to avoid hot spots.

The process according to the invention, and the particular embodiments thereof, preferably comprises carrying out the reaction of the first step according to this specific aspect.

The elimination of hydrogen halide in the second step can be performed by warming up the reaction medium to a range as indicated above.

A preferred aspect of the process according to the present invention comprises the following steps:
providing the halogenated precursor of the alkenone by manufacture from a carboxylic acid halide and a vinyl ether in accordance with any of the various aspects and embodiments of the first step disclosed herein before or a combination thereof (such as step (a), step (a'), step (a"), or combinations thereof);
(b') eliminating the hydrogen halide from said precursor obtained in the first step (such as step (a), step (a'), step (a") or combinations thereof) to form the alkenone, wherein said hydrogen halide elimination comprises at least one thermolysis treatment selected from the group consisting of a flash thermolysis, a vacuum thermolysis, and a thermolysis under stripping with an inert gas; and/or
(b") eliminating hydrogen halide from said halogenated precursor obtained in the first step (such as step (a), step (a'), step (a") or combinations thereof) to form an alkenone, wherein said hydrogen halide elimination comprises a thermolysis treatment carried out at a temperature from greater than 90° C. to 120° C.

It has been found, surprisingly, that the process according to the invention, in particular a flash thermolysis, allows for high conversion of the halogenated precursor of the alkenone, under productive conditions. The process according to the invention also allows for particularly high selectivity, including configuration isomer selectivity, to alkenone, in particular ETFBO. The high selectivity allows further for simplified purification and high isolated yield of the target product.

In the second process step, two or more thermolysis treatments may be combined. For example, thermolysis can be carried out at a temperature from greater than 90° C. to 120° C. under stripping with inert gas; or a vacuum thermolysis may be combined with stripping with inert gas.

A vacuum thermolysis in step (b') may be carried out at a temperature from 60° C. to 140° C.

The thermolysis treatment in step (b') may comprise a vacuum thermolysis carried out at a temperature of from 60° C. to 130° C.

Thermolysis in the sense of the second step according to the present invention can suitably be carried out by heating a liquid fraction comprising halogenated precursor to the temperature of the thermolysis treatment. Heating can be carried out by suitable means such as in particular contacting the liquid fraction with a heated solid body such as for example, the walls of a reactor, a heat exchanger and a heated pipe. Heating can also be carried out by providing a hot gas, in particular a hot inert gas such as in particular nitrogen to the liquid fraction.

The thermolysis in the process according to the invention is suitably carried out in an apparatus facilitating withdrawal of formed gaseous hydrogen halide from the liquid fraction. Often, such apparatus include means for increasing the surface of the liquid fraction. "Means for increasing the surface of the liquid fraction" is understood to denote in particular any means which provides an increased surface of the liquid fraction in contact with a gas phase when compared with the surface which is in contact with a gas phase of the same volume of liquid fraction when filled into a spherical flask having double volume of the liquid phase. Particular examples of such apparatus include film evaporators and, preferably columns having a flow resistance. Use may be made, for example, of plate columns or plate columns of dual-flow type or preferably of columns with bulk or structured packing. Particular examples of suitable columns are packed, for example with Pall or preferably Raschig rings.

The means for increasing the surface of the liquid fraction is generally connected to at least one line allowing for withdrawal of a gas stream, in particular a hydrogen halide stream. If desired such line may also be used to apply a vacuum, in particular as described herein. The means for increasing the surface of the liquid fraction may be connected, if desired, to at least one line allowing for supply of inert gas in particular as described herein.

When a means for increasing the surface of the liquid fraction is used, heating of the liquid fraction may be suitably provided externally, for example by circulating the liquid fraction between the means for increasing the surface of the liquid fraction and a means for heating, in particular as described above, preferably a heat exchanger.

The temperature of the thermolysis treatment is often at least 50° C., often equal to or greater than 60° C., preferably equal to or greater than 70° C. preferably equal to or greater than about 80° C. The temperature of the thermolysis treatment is generally less than 150° C., often less than or equal to 140° C., preferably less than or equal to 130° C. A thermolysis treatment carried out at a temperature from greater than 90° C. to 120° C., in particular about 100° C. is particularly preferred. It has been found that this temperature range is particularly efficient, in particular for thermolysis of CETFBO to ETFBO.

For the purpose of the present invention, the term "flash thermolysis" refers to a process wherein the liquid reaction medium is heated up in a short time. Typical heating times for flash thermolysis are less than 1 hour, in particular less than 30 minutes, preferably about 15 minutes. Generally, the heating time is greater than 1 s, often greater than 15 s.

"Heating time" is understood to denote in particular the time required to heat the liquid fraction containing halogenated precursor, in particular a liquid reaction medium, from an initial temperature to the temperature of the thermolysis treatment. A typical initial temperature is less than 50° C., often less than 40° C., preferably equal to or less than 30° C. In one aspect, the temperature is preferably equal to or less than about −25° C. The initial temperature is generally at least −50° C., often equal to or greater than −40° C., preferably equal to or greater than −30° C. Often, the initial temperature corresponds to the temperature with which the alkenone precursor leaves its manufacturing process. In an stirred tank reactor, for example, the reaction temperature for the addition of the acid halide to a vinyl ether is often carried out at a temperature from 0° C. to 40° C. Consequently, the initial temperature of the precursor is also in that range.

In particular aspects of the second process step according to this embodiment, the flash thermolysis is conducted at a temperature ranging from −20° C. to 140° C. and a period of time ranging from 30 seconds to 1 hour, preferably at a temperature ranging from 0° C. to 130° C. and a period of time ranging from 30 seconds to 30 minutes, more preferably at a temperature ranging from 20° C. to 120° C. and a period of time ranging from 30 seconds to 20 minutes.

An additional advantage of the flash thermolysis is that the formation of the Hetero-Diels-Alder product of 2 molecules of the alkenone, especially when ETFBO is prepared, is avoided. The Hetero-Diels-Alder product is increasingly formed if the thermolysis is performed in a too long time range.

The thermolysis or flash thermolysis can be optionally carried out under stripping with an inert gas stream such as nitrogen gas, argon gas. For the purpose of the present invention, the term "stripping" denotes in particular a physical separation process where one or more components, in particular HCl, are removed from the liquid reaction medium by a gas stream. The liquid and gas streams can have concurrent or countercurrent flow directions.

If appropriate, the stripping is advantageously carried out with a nitrogen stream.

The second step in the process according to this embodiment generally comprises carrying out a thermolysis at a temperature of −20° C. to 140° C., preferably from 60 to 130° C., for example at equal to or about 80° C. and more preferably at equal to or about 120° C. Preferably thermolysis in the second process step may be carried out at a temperature from greater than 90° C. to 120° C.

The thermolysis or flash thermolysis may be carried out under vacuum. In that case, the vacuum is preferably from 100 to 600 mbar, preferably from 100 mbar to lower than 500 mbar, for example from 200 to 450 mbar.

It is understood that the different steps and embodiments disclosed herein apply in most preferred way to the manufacture of chlorotrifluoroalkoxybutanone from alkyl-vinylether and trifluoroacetic acid halide, in particular from trifluoroacetyl chloride and ethyl vinyl ether and subsequent elimination to form trifluoroalkoxybutenone, in particular ETFBO.

It is understood that the different steps and embodiments disclosed herein apply in most preferred way to the manufacture of chlorodifluoroalkoxybutanone from alkyl-vinylether and difluoroacetic acid halide, in particular from difluoroacetyl chloride and ethyl vinyl ether and subsequent elimination to form difluoroalkoxybutenone, in particular EDFBO.

Furthermore, the present invention also relates to a process for preparing an alkenone and also an apparatus for preparing a halogenated precursor of an alkenone, for example using the above apparatus.

In such process, previously produced pure organic product, for example ETFBO, is circulated to start up and is cooled, optionally with the help of a cooling machine. When the respective target temperature is reached, the first reactant (for example TFAC) is first of all fed in gaseous or liquid form, before the first reactor, into the circuit (in particular turbulent circuit) and then the second reactant (for example EVE) is added in slight stoichiometric excess (for example, TFAC:EVE=1:1.01 mol). The level in the flask of the circulation means is kept constant by operating a membrane pump and discharging into the second means. In which, conversion of organic products' precursors to the organic products with the elimination of hydrogen halide, for example conversion of CETFBO into ETFBO with HCl elimination, either takes place by in batches (in particular thermolysis) once the receiver of the second means is full or by continuously feeding the organic products' precursors (e.g., CETFBO) stream from the circulation means into the second means, which is then under an optional slight vacuum. Precision distillation then takes place continuously or in batches in a further distillation column downstream.

The third step in the process for synthesizing a chemical according to the present invention comprises:
(c) using the alkenone as a building block to synthesize the chemical.

The alkenone used in step (c) is formed in the second step of the process according to the present invention. The second process step may be any of the various aspects and embodiments of the second step disclosed herein, such as step (b), step (b'), step (b''), or combinations thereof.

The alkenone which can be prepared from the halogenated alkenone precursor of formula (I) via the second step is preferably the alkenone of formula (IV), $$R^1\text{---}C(O)\text{---}CH=CH\text{---}OR^2 \qquad (IV)$$

wherein $R^1$ and $R^2$ have the same meaning as in formula (I).

In preferred embodiments, $R^1$ is a fluorinated C1-C4 alkyl group, and wherein $R^2$ is a C1-C4 alkyl group.

In preferred embodiments, the chemical synthesized in step (c) is an agriculturally active compound or a pharmaceutically active compound. In such instances, step (c) preferably comprises converting said alkenone obtained in the second step (e.g., step (b), step (b'), step (b"), or combinations thereof) into such agriculturally active or pharmaceutically active compound.

As used herein in the present description, an "agriculturally active compound" is a chemical that improves the quantity and/or quality of agricultural products in the production of crops. Non-limiting examples of "agriculturally active compound" may be selected from the group consisting of fertilizer, hormone, fungicide, herbicide, miticides, germination enhancer, growth enhancing agent, algaecides, nematicides, insect attractants, repellants, pheromones, modifiers of plant physiology or structure, herbicide safeners, biocides, termiticides, rodenticides, arthropodicides, insecticides, and compounds for soil treatment. Typical applications of such "agriculturally active compound" include agricultural, horticultural, pest management, home and garden and forestry applications.

As used herein in the present description, the term "pharmaceutically active compound" is intended to denote a compound intended for use in medical diagnosis, cure, treatment, or prevention of disease, or intended to be used to otherwise enhance physical or mental well-being. Non-limiting examples of such term "pharmaceutically active compound" include serine protease inhibitors, modulators of dopamine D3 receptors, cannabinoid receptor 1 antagonists, Vanilloid Receptor Ligands, compounds that inhibit or modulate the activity of Cyclin Dependent Kinases (CDK), Glycogen Synthase Kinases (GSK) and Aurora kinases, TRPV1 antagonists, compounds for the treatment of diseases associated with cellular proliferation, inflammation, or glycosidase expression, inhibition of store-operated $Ca^{2+}$ (SOC) channel activity, compounds for treatment of Hepatitis C, pain, traumatic injury, schizophrenia, Alzheimers disease or other neurological and/or psychiatric disorders.

In preferred embodiments for the third step, the conversion of such alkenone in step (c) comprises:
  reacting the alkenone with a nitrogen-containing compound selected from the group consisting of hydrazine, hydrazine hydrate, hydrazine hydrochloride, methylhydrazine, methylhydrazine hydrate, methylhydrazine hydrochloride, ethylhydrazine, ethylhydrazine hydrate, ethylhydrazine hydrochloride, hydroxylamine, hydroxylamine hydrate, hydroxylamine hydrochloride, urea, thiourea, malonic acid monoamide, malonic acid diamide, 2-phenylcarbamoylacetic acid ester, propen-1-enyl-pyrrolidine, acetoacetamide, dimethylmalondiamide, 3-amino-3-iminopropanoate, 3-oxo-1,2-pyrazolidinium ylides, semicarbazide-hydrochloride, ethyl 4-(pyrrolidin-1yl)cyclohex-3-ene-1-carboxylate, imidamides, substituted acetonitriles, and malonic acid mononitrile.

An example for the reaction of an alkenone with hydrazine or hydrazine hydrochloride to yield the corresponding pyrazole can be found in U.S. Pat. No. 8,431,710 and US2006/128702 (hydrazine hydrochloride), both incorporated herein by reference.

An example for the reaction of an alkenone with urea to yield the corresponding pyrimidine-2-one can be found in U.S. Pat. No. 8,431,710. The alkenone may be reacted with alkylated hydrazines to form the corresponding pyridines.

An example for the reaction of an alkenone with ethylhydrazine to yield the corresponding pyridine can be found in US2012/53210, incorporated herein by reference.

Similarly, an example for the reaction of an alkenone with methylhydrazine to yield the corresponding pyridine can be found in US2011/071291, incorporated herein by reference.

An example for the reaction of an alkenone with malonic acid monoamide, such as methylmalonamide or ethylmalonamide to yield the corresponding pyridine can be found in U.S. Pat. No. 8,431,710.

An example for the reaction of an alkenone with 2-phenylcarbamoylacetic acid ethyl ester to yield the corresponding pyridine can be found in U.S. Pat. No. 8,076,487, incorporated herein by reference.

An example for the reaction of an alkenone with thiourea to yield the corresponding pyridine can be found in U.S. Pat. No. 8,076,487.

An example for the reaction of an alkenone with propen-1-enyl-pyrrolidine in the presence of an ammonium salt to yield the corresponding pyridine can be found in US2009/029863, incorporated herein by reference. Similarly, ethyl 4-(pyrrolidin-1yl)cyclohex-3-ene-1-carboxylate can be reacted with the alkenone to give the quinoline derivative as described in US2011/021514, incorporated herein by reference.

An example for the reaction of an alkenone with acetoacetamide to yield the corresponding pyridinone can be found in US2013/172334, incorporated herein by reference.

Examples for the reaction of an alkenone with dialkyl malonic acid diamides, e.g., dimethylmalondiamide to yield the corresponding pyridine can be found in U.S. Pat. No. 8,076,487 and US2010/222592, incorporated herein by reference.

An example for the reaction of an alkenone with 3-amino-3-iminopropanoate to yield the corresponding pyridine can be found in US2011/287937, incorporated herein by reference.

An example for the reaction of an alkenone with 3-oxo-1,2-pyrazolidinium ylides to yield the corresponding bicyclic pyrazolidinones can be found in Y. Xin et al, J. of Fluorine Chemistry, 2011, vol. 132(6), pp. 402-408, incorporated herein by reference.

An example for the reaction of an alkenone with 2,4-pentadione to yield the corresponding phenylderivative can be found in US2004/224960, incorporated herein by reference.

An example for the reaction of an alkenone with semicarbazide-hydrochloride to yield the corresponding pyrazolecarboxamide derivative can be found in P. Sauzem et al, Europ. J. Med. Chem., 2008, vol. 43(6), pp. 1237-1257, incorporated herein by reference.

An example for the reaction of an alkenone with imidamides such as 5-hexenimidamide to yield the corresponding pyrimidine can be found in US2009/221618, incorporated herein by reference.

An example for the reaction of an alkenone with substituted acetonitriles such as chloroacetonitrile to yield the corresponding pyridone can be found in US2009/318455, incorporated herein by reference.

An example for the reaction of an alkenone with hydroxylamine hydrochloride to yield the corresponding dihydroisoxazoles can be found in A. Colla et al, Synthesis, 1991, vol. 6, pp. 483-486, incorporated herein by reference.

The term 'comprising' also includes "consisting essentially of" and also "consisting of".

Any reference to 'an' element is understood to encompass 'one or more' elements. The use of the singular 'a' or 'one' herein includes the plural (and vice versa) unless specifically stated otherwise.

In the present application, where an element or component is said to be included in and/or selected from a list of recited elements or components, it should be understood that in related embodiments explicitly contemplated here, the element or component can also be any one of the individual recited elements or components, or can also be selected from a group consisting of any two or more of the explicitly listed elements or components, or any element or component recited in a list of recited elements or components may be omitted from this list. Further, it should be understood that elements and/or features of compositions, processes or methods described herein can be combined in a variety of ways without departing from the scope and disclosures of the present teachings, whether explicit or implicit herein.

The disclosure of all patent applications, and publications cited herein are hereby incorporated by reference, to the extent that they provide exemplary, procedural or other details supplementary to those set forth herein.

Should the disclosure of any of the patents, patent applications, and publications that are incorporated herein by reference conflict with the present specification to the extent that it might render a term unclear, the present specification shall take precedence.

EXAMPLES

The examples hereafter are intended to illustrate the invention without however limiting it.

In these examples and throughout this specification the abbreviations employed are defined as follows: TFAC is trifluoroacetylchloride, EVE is ethyl vinyl ether, CETFBO is 4-Chloro-4-Ethoxy-1,1,1-trifluoro-3-butan-2-one, ETFBO is Ethoxy-1,1,1-trifluoro-3-buten-2-one.

Example 1

Two-step manufacture of 4-Ethoxy-1,1,1-trifluoro-3-buten-2-one

First Step:

In a 100 ml three-necked flask surmounted by a dry-ice cooler, equipped with a Pt100 internal thermometer 66.24 g (0.5 mole) trifluoroacetylchloride was condensed in at −30° C. 36.06 g (0.5 mole) of ethyl vinyl ether was added dropwise over 1 hour. After the addition, further 0.5 mole trifluoroacetylchloride was added. GC of a sample showed almost quantitative yield of 4-Chloro-4-Ethoxy-1,1,1-trifluoro-3-butan-2-one.

Second Step:

After the reaction of the first step described above, the flask was warmed to room temperature and subjected to fractional distillation in vacuo. A first fraction (B.P. 59.3-66.4° C. at 47 mbar) contained a mixture of 4-Chloro-4-Ethoxy-1,1,1-trifluoro-3-butan-2-one and 4-Ethoxy-1,1,1-trifluoro-3-buten-2-one, which could be redistilled to provide further 4-Ethoxy-1,1,1-trifluoro-3-buten-2-one. A second fraction (B.P. 66.4-70° C. at 30 mbar) contained pure Ethoxy-1,1,1-trifluoro-3-buten-2-one (E/Z ratio 98.5:1.5). The isolated yield was 97.5% of theoretical yield.

Example 2

Manufacture of 4-Chloro-4-Ethoxy-1,1,1-trifluoro-3-butane-2-one and 4-Ethoxy-1,1,1-trifluoro-3-butene-2-one under turbulent conditions and ETFBO as solvent General procedure: Pure ETFBO, obtained by a previous synthesis, was placed into the flow part of a recirculation system and cooled using a chiller. This recirculation system comprises a 20-L flask, 2 one-meter distillation columns filled with 10-mm glass Raschig rings placed on top of another distillation column, a circulation pump (1500 l/h), 3 tube reactors each with 3-m path length (diameter of 1.5 cm). Once the desired temperature was reached in the recirculation system, gaseous or liquid trifluoroacetylchloride (15 kg/h; 113.2 mol/h) was introduced in the turbulent circulation in front of the first 3 m reactor and then a small molar excess of ethyl vinyl ether (TFAC/EVE=1:1.01) was added after the first 3 m reactor. The level in the 20-L flask of the recycle apparatus was kept constant by pumping material using a membrane pump into a second apparatus. This second apparatus which serves for the thermolysis of 4-Chloro-4-Ethoxy-1,1,1-trifluoro-3-butan-2-one (CETFBO) to 4-Ethoxy-1,1,1-trifluoro-3-buten-2-one (ETFBO), comprises a 100-L Pfaudler ceramic vessel with 3 one-meter distillation columns filled with 10-mm glass Raschig rings and a cooler with removal. The conversion of CETFBO to ETFBO under loss of HCl takes place either through batchwise thermolysis when the ceramic vessel is full or through continuous feeding of the CETFBO stream from the recycle apparatus. The fine distillation was further carried out continuously or batchwise in the distillation columns.

Example 2a

The recirculation system was filled with pure ETFBO and cooled to a temperature of 10° C. Following the general procedure, TFAC and EVE were introduced at a rate of 12.4 mol/h and 12.8 mol/h, respectively. A GC sample taken every hour at the top of the recycle apparatus, showed a complete reaction from TFAC with EVE whereby the CETFBO concentration was increasing continuously with a decreasing of the ETFBO concentration. The continuous introduction of TFAC and EVE was carried out during 8 hours and all the material was collected in the ceramic vessel. The thermolysis was carried out at 80° C. under a nitrogen stream, followed by a fractional distillation to provide 4-Ethoxy-1,1,1-trifluoro-3-buten-2-one in an isolated yield of 87% of the theoretical yield and with a purity (cis+trans isomer) of 98%.

Example 2b

The same procedure was followed as Example 2a but the recirculation system was kept at a temperature of 20° C. Ethoxy-1,1,1-trifluoro-3-buten-2-one was obtained in an isolated yield of 87% of the theoretical yield and with a purity (cis+trans isomer) of 98%.

Example 3

Conversion of CETFBO to ETFBO by Thermolysis Treatment

General procedure: After the reaction of the first step as described above in Example 1, the flask, fitted with a reflux condenser, was heated to the desired temperature by using an oil bath. The thermolysis or flash thermolysis was performed under different conditions: at different temperatures, with or without an inert gas stream or under vacuum. The conversion of CETFBO to ETFBO was followed by GC analyses. When the composition of the reaction mixture remained constant, the resulting reaction mixture was further subjected to a distillation in vacuo (70° C., 20 mbar) to obtain Ethoxy-1,1,1-trifluoro-3-buten-2-one. The experimental data are summarized in Table 1. The thermolysis time refers to the time after which the composition of the reaction mixture remained constant.

TABLE 1

| Example | Conditions | Thermolysis time [min] | % wt of CETFBO | % wt of ETFBO (cis/trans) | Isolated yield of ETFBO (%) |
|---------|------------|------------------------|----------------|----------------------------|------------------------------|
| 3a | 80° C. | 43 | 5.2 | 88.9/1.3 | 85.7 |
| 3b | 80° C./N$_2$ stream (24 l/h) | 80 | 0.3 | 97.6/1.6 | 91.5 |
| 3c | 80° C./vacuum (400 mbar) | 80 | 1.4 | 95.1/1.7 | 89.3 |
| 3d | 120° C. | 17 | 1.2 | 94.3/1.4 | 89.9 |
| 3e | flash thermolysis 120° C. | 13 | 1.0 | 94.9/1.5 | 93.0 |
| 3f | flash thermolysis 100° C. | 25 | 2.8 | 93.7/1.4 | 93.7 |

The % wt of CETFBO and % wt of ETFBO (cis/trans) were measured by GC analyses.

Example 4

Reaction

1$^{st}$ Step: Production of 4-chloro-4-ethoxy-1,1,1-trifluorobutane-2-one (CETFBO)

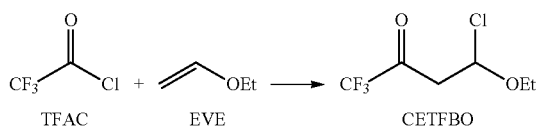

2$^{nd}$ Step: Production of 4-ethoxy-1,1,1-trifluoro-3-butene-2-one (ETFBO)

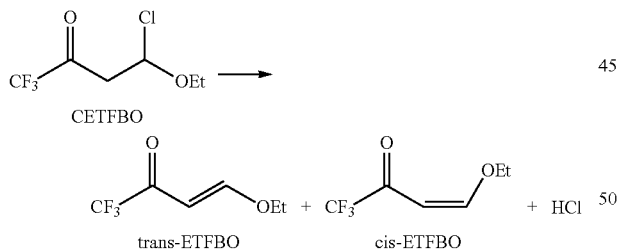

Charge:

| ETFBO | 0.700 mol | 119 g | 76.9% by weight |
|-------|-----------|-------|------------------|
| TFAC  | 0.175 mol | 23.3 g | 15.0% by weight |
| EVE   | 0.175 mol | 12.6 g | 8.1% by weight |

119 g (0.7 mol) ETFBO were presented in a three-necked flask with dry-ice cooler and magnetic agitator and were cooled to 0° C. 23.3 g (0.175 mol) TFAC were introduced from a pressure flask. TFAC dissolved very easily in ETFBO. Then 12.6 g (0.175 mol) EVE was added all at once. A first sample was taken (GC analysis, WLD detector) after 21 minutes. There were still 2 GC-% TFAC in the mixture. After 60 minutes all the TFAC was converted. Thermolysis was then carried out for 1 hour at 80° C., until no more HCl escaped and the batch was fractionally precision distilled in a vacuum at 10$^{-3}$ mbar. The ETFBO yield thus isolated amounted to 97% and the purity was 99.5% (98.0% trans-isomer, 1.5% cis-isomer).

Example 5

Pure ETFBO was poured into the circulation apparatus and the temperature was adjusted to +10° C. TFAC was then added at a rate of 12.4 mol/h and EVE at a rate of 12.8 mol/h. GC samples taken hourly from the bottom of the circulation apparatus indicated complete conversion of TFAC with EVE. The concentration of the circulating CETFBO rose continuously, while the ETFBO concentration decreased continuously. The apparatus was operated under these conditions for 8 hours and the material was collected in the second apparatus. Subsequent thermolysis at 80° C. in a nitrogen stream to eliminate the HCl, followed by fractional precision distillation produced ETFBO in an isolated yield of 87% of the theoretical and a purity (cis+trans isomer) of 98.0%.

Example 6

The experiment was repeated as described in Example 5 except that the temperature was +20° C. The selectivity and isolated yield were comparable with the experiment at +10° C.

We claim:

1. A process for synthesizing a chemical, comprising the following steps:
    carrying out a first step to prepare a halogenated precursor of an alkenone, said first step comprising at least one step selected from the group consisting of:
    (a) reacting a carboxylic acid halide with a vinyl ether in a liquid reaction medium to prepare said halogenated precursor of an alkenone, wherein at least a part of said carboxylic acid halide is introduced in liquid state into said reaction medium, wherein said reaction is carried out under conditions of pressure and temperature under which said carboxylic acid halide is gaseous, and wherein, when the liquid carboxylic acid halide gets into the gaseous state in the liquid reaction medium, gas bubbles are generated in the liquid reaction medium to provide the reaction medium in turbulent state; and
    (a') reacting a carboxylic acid halide with a vinyl ether in a liquid reaction medium comprising an alkenone or a halogenated precursor of an alkenone;
    (b) eliminating hydrogen halide from said halogenated precursor of the alkenone formed in the first step to form the alkenone; and
    (c) using said alkenone as a building block to synthesize said chemical by reacting said alkenone with a nitrogen-containing compound;
    wherein said chemical is an agriculturally active compound or a pharmaceutically active compound; and wherein step (c) comprises converting said alkenone obtained in step (b) into said agriculturally active or pharmaceutically active compound.

2. The process according to claim 1, wherein step (a) is carried out in the first step.

3. The process according to claim 1, wherein step (a') is carried out in the first step.

4. The process according to claim 1, wherein the halogenated precursor of the alkenone corresponds to Formula (I): R$^1$—C(O)—CH2-CH(X)—OR$^2$ (I), wherein X represents fluorine, chlorine, or bromine; $R^1$ represents a C1-C10 alkyl group which is optionally substituted by at least one halogen atom or $R^1$ represents CF3C(O)CH2; and $R^2$ represents aryl, substituted aryl, or a C1-C10 alkyl group which is optionally substituted by at least one halogen atom; wherein the acid halide corresponds to Formula (II): $R^1$—C(O)X (II) in which X and $R^1$ has the same meaning as in Formula (I); and wherein the vinyl ether corresponds to Formula (III): CH2=C(H)—$OR^2$ (III) in which $R^2$ has the same meaning as in Formula (I).

5. The process according to claim 4, wherein $R^1$ is a fluorinated C1-C4 alkyl group, and wherein $R^2$ is a C1-C4 alkyl group.

6. The process according to claim 1, wherein the carboxylic acid halide is trifluoroacetyl chloride.

7. The process according to claim 1, wherein the elimination of hydrogen halide from said halogenated precursor of the alkenone obtained in the first step to form said alkenone comprises at least one thermolysis treatment selected from the group consisting of a flash thermolysis, vacuum thermolysis, and thermolysis under stripping with inert gas.

8. The process according to claim 7, wherein the at least one thermolysis treatment comprises a vacuum thermolysis carried out at a temperature from 60° C. to 130° C.

9. The process according to claim 1, wherein
said nitrogen-containing compound is selected from the group consisting of hydrazine, hydrazine hydrate, hydrazine hydrochloride, methylhydrazine, methylhydrazine hydrate, methylhydrazine hydrochloride, ethylhydrazine, ethylhydrazine hydrate, ethylhydrazine hydrochloride, hydroxylamine, hydroxylamine hydrate, hydroxylamine hydrochloride, urea, thiourea, malonic acid monoamide, malonic acid diamide, 2-phenylcarbamoylacetic acid ester, propen-1-enyl-pyrrolidine, acetoacetamide, dimethylmalondiamide, 3-amino-3-iminopropanoate, 3-oxo-1,2-pyrazolidinium ylides, semicarbazide-hydrochloride, ethyl 4-(pyrrolidin-1yl) cyclohex-3-ene-1-carboxylate, imidamides, substituted acetonitriles, and malonic acid mononitrile.

10. A process for synthesizing a chemical, comprising the following steps:
(a") preparing a halogenated precursor of an alkenone corresponding to Formula (I): $R^1$—C(O)—CH2-CH(X)—$OR^2$ (I), wherein X represents fluorine, chlorine or bromine and $R^1$ represents a C1-C10 alkyl group which is optionally substituted by at least one halogen atom or $R^1$ represents CF3C(O)CH2; and $R^2$ represents aryl, substituted aryl, or a C1-C10 alkyl group which is optionally substituted by at least one halogen atom; wherein an acid halide corresponding to Formula (II): $R^1$—C(O)X (II) in which X and $R^1$ has the same meaning as in Formula (I) is reacted with a vinyl ether corresponding to Formula (III): CH2=C(H)—$OR^2$ (III) in which $R^2$ has the same meaning as in Formula (I), to form said halogenated precursor;
(b') eliminating hydrogen halide from said halogenated precursor of the alkenone formed in step (a") to form the alkenone, wherein the elimination of hydrogen halide comprises at least one thermolysis treatment selected from the group consisting of a flash thermolysis, vacuum thermolysis, and thermolysis under stripping with inert gas; and
(c) using said alkenone as a building block to synthesize said chemical by reacting said alkenone with a nitrogen-containing compound;
wherein said chemical is an agriculturally active compound or a pharmaceutically active compound; and wherein step (c) comprises converting said alkenone obtained in step (b') into said agriculturally active or pharmaceutically active compound.

11. The process according to claim 10, wherein $R^1$ is a fluorinated C1-C4 alkyl group, and wherein $R^2$ is a C1-C4 alkyl group.

12. The process according to claim 10, wherein said carboxylic acid halide is trifluoroacetyl chloride.

13. The process according to claim 10, wherein
said nitrogen-containing compound is selected from the group consisting of hydrazine, hydrazine hydrate, hydrazine hydrochloride, methylhydrazine, methylhydrazine hydrate, methylhydrazine hydrochloride, ethylhydrazine, ethylhydrazine hydrate, ethylhydrazine hydrochloride, hydroxylamine, hydroxylamine hydrate, hydroxylamine hydrochloride, urea, thiourea, malonic acid monoamide, malonic acid diamide, 2-phenylcarbamoylacetic acid ester, propen-1-enyl-pyrrolidine, acetoacetamide, dimethylmalondiamide, 3-amino-3-iminopropanoate, 3-oxo-1,2-pyrazolidinium ylides, semicarbazide-hydrochloride, ethyl 4-(pyrrolidin-1yl) cyclohex-3-ene-1-carboxylate, imidamides, substituted acetonitriles, and malonic acid mononitrile.

14. A process for synthesizing a chemical, comprising the following steps:
a") preparing a halogenated precursor of an alkenone, said halogenated precursor corresponding to Formula (I): $R^1$—C(O)—CH2-CH(X)—$OR^2$ (I), wherein X is fluorine, chlorine, or bromine; $R^1$ represents a C1-C10 alkyl group which is optionally substituted by at least one halogen atom or represents CF3C(O)CH2; and $R^2$ represents aryl, substituted aryl, or a C1-C10 alkyl group which is optionally substituted by at least one halogen atom, said step (a") comprising reacting an acid halide corresponding to Formula (II): $R^1$—C(O)X (II) in which X and $R^1$ has the same meaning as in Formula (I), with a vinyl ether corresponding to Formula (III): CH2=C(H)—$OR^2$ (III) in which $R^2$ has the same meaning as in Formula (I), to form said halogenated precursor;
b") eliminating hydrogen halide from said halogenated precursor obtained in step (a") to form an alkenone, wherein said hydrogen halide elimination comprises a thermolysis treatment carried out at a temperature from greater than 90° C. to 120° C.; and
c) using said alkenone as a building block to synthesize said chemical by reacting said alkenone with a nitrogen-containing compound;
wherein said chemical is an agriculturally active compound or a pharmaceutically active compound; and wherein step (c) comprises converting said alkenone obtained in step (b") into said agriculturally active or pharmaceutically active compound.

15. The process according to claim 14, wherein $R^1$ is a fluorinated C1-C4 alkyl group, and wherein $R^2$ is a C1-C4 alkyl group.

16. The process according to claim 14, wherein said carboxylic acid halide is trifluoroacetyl chloride.

17. The process according to claim 14, wherein
said nitrogen-containing compound is selected from the group consisting of hydrazine, hydrazine hydrate, hydrazine hydrochloride, methylhydrazine, methylhydrazine hydrate, methylhydrazine hydrochloride, ethylhydrazine, ethylhydrazine hydrate, ethylhydrazine hydrochloride, hydroxylamine, hydroxylamine hydrate, hydroxylamine hydrochloride, urea, thiourea, malonic acid monoamide, malonic acid diamide, 2-phenylcarbamoylacetic acid ester, propen-1-enyl-pyrrolidine, acetoacetamide, dimethylmalondiamide, 3-amino-3- iminopropanoate, 3-oxo-1,2-pyrazolidinium ylides, semicarbazide-hydrochloride, ethyl 4-(pyrrolidin-1yl) cyclohex-3-ene-1-carboxylate, imidamides, substituted acetonitriles, and malonic acid mononitrile.

* * * * *